United States Patent
Graumann et al.

(10) Patent No.: US 11,284,846 B2
(45) Date of Patent: Mar. 29, 2022

(54) METHOD FOR LOCALIZATION AND IDENTIFICATION OF STRUCTURES IN PROJECTION IMAGES

(75) Inventors: Rainer Graumann, Hoechstadt (DE); Gerhard Kleinszig, Erlangen (DE); Yoshito Otake, Baltimore, MD (US); Jeffrey Siewerdsen, Baltimore, MD (US)

(73) Assignees: The John Hopkins University, Baltimore, MD (US); Siemens Aktiengesellschaft, Munich (DE)

( * ) Notice: Subject to any disclaimer, the term of this patent is extended or adjusted under 35 U.S.C. 154(b) by 1049 days.

(21) Appl. No.: 13/285,493

(22) Filed: Oct. 31, 2011

(65) Prior Publication Data
US 2012/0289826 A1    Nov. 15, 2012

Related U.S. Application Data

(60) Provisional application No. 61/485,578, filed on May 12, 2011.

(51) Int. Cl.
 *A61B 6/03*     (2006.01)
 *A61B 6/00*     (2006.01)
 (Continued)

(52) U.S. Cl.
 CPC ............ *A61B 6/032* (2013.01); *A61B 6/12* (2013.01); *A61B 6/487* (2013.01); *A61B 6/5235* (2013.01);
 (Continued)

(58) Field of Classification Search
 CPC ......... A61B 6/032; A61B 6/12; A61B 6/4441; A61B 6/487; A61B 6/504; A61B 6/505;
 (Continued)

(56) References Cited

U.S. PATENT DOCUMENTS 7,689,019 B2 *   3/2010  Boese et al. .............. 382/128
7,831,074 B2 *  11/2010  Zhou et al. ............... 382/128
(Continued)

OTHER PUBLICATIONS

Zollei, "2D-3D Rigid-Body Registration of X-Ray Fluoroscopy and CT Images", Masters Thesis, MIT AI Lab, Aug. 2001.*
(Continued)

*Primary Examiner* — Katherine L Fernandez
(74) *Attorney, Agent, or Firm* — Laurence A. Greenberg; Werner H. Stemer; Ralph E. Locher

(57) ABSTRACT

A method for localization and identification of a structure in a projection image with a system having a known system geometry, includes acquiring a preoperative computer-tomography or CT image of a structure, preprocessing the CT-image to a volume image, acquiring an intraoperative two dimensional or 2D X-ray image, preprocessing the 2D X-ray image to a fix image, estimating an approximate pose of the structure, calculating a digitally reconstructed radiograph or DRR using the volume image, the estimated pose and the system geometry, and calculating a correlation between the generated DRR and the fix image, with a correlation value representing matching between the generated DRR and the fix image. The method significantly decreases the number of wrong-level surgeries and is independent of the surgeon's ability to localize and/or identify a target level in a body.

3 Claims, 2 Drawing Sheets

(51) Int. Cl.
*A61B 6/12* (2006.01)
*G06T 7/32* (2017.01)

(52) U.S. Cl.
CPC .............. *G06T 7/32* (2017.01); *A61B 6/4441* (2013.01); *A61B 6/504* (2013.01); *A61B 6/505* (2013.01); *A61B 6/506* (2013.01); *G06T 2207/10081* (2013.01); *G06T 2207/10116* (2013.01); *G06T 2207/10121* (2013.01); *G06T 2207/10124* (2013.01); *G06T 2207/30012* (2013.01)

(58) Field of Classification Search
CPC .................. A61B 6/506; A61B 6/5235; G06T 2207/10081; G06T 2207/10116; G06T 2207/10121; G06T 2207/10124; G06T 2207/30012; G06T 7/0026
USPC .................................. 600/425; 382/128, 131
See application file for complete search history.

(56) References Cited

U.S. PATENT DOCUMENTS

| | | | |
|---|---|---|---|
| 2002/0065461 A1* | 5/2002 | Cosman | 600/426 |
| 2004/0120449 A1* | 6/2004 | Edic | A61B 6/032 378/4 |
| 2006/0188139 A1* | 8/2006 | Khamene et al. | 382/130 |
| 2006/0204063 A1* | 9/2006 | Nakashima et al. | 382/128 |
| 2007/0003117 A1* | 1/2007 | Wheeler et al. | 382/128 |
| 2008/0037843 A1* | 2/2008 | Fu | G06T 15/08 382/128 |
| 2009/0003523 A1* | 1/2009 | Raanes et al. | 378/65 |

OTHER PUBLICATIONS

Mody et al., "The prevalence of wrong level surgery among spine surgeons," Spine vol. 33, No. 2, 2008, pp. 194-198.

Perisinakis et al., "Estimation of patient dose and associated radiogenic risks from fluoroscopically guided pedicle screw insertion," Spine, vol. 29, No. 14, 2004, pp. 1555-1560.

Mariscalco et al., "Radiation exposure to the surgeon during open lumbar microdiscectomy and minimally invasive microdiscectomy: a prospective, controlled trial," Spine, vol. 36, No. 3, 2011, pp. 255-260.

Singh et al., "Novel fluoroscopic technique for localization at cervicothoracic levels," J.Spinal.Disord.Tech.,vol. 22, No. 8, 2009, pp. 615-618.

Markelj et al., "A review of 3D/2D registration methods for image-guided interventions," Medical Image Analysis 2010, Article in Press, Elsevier journal homepage: www.elsevier.com/locate/media.

Fu et al., "A fast, accurate, and automatic 2D-3D image registration for image-guided cranial radiosurgery," Med. Phys. May 35(5), May 2008, pp. 2180-2194.

Agazaryan et al., "Image-guided radiosurgery for spinal tumors: methods, accuracy and patient intrafraction motion," Physic in Medicine and Biology, vol. 53, No. 6, 2008, pp. 1715-1727.

Prince et al., "Medical imaging signals and systems", Pearson Prentice Hall, 2006, Upper Saddle River, N.J.

Pluim et al., "Image registration by maximization of combined mutual information and gradient information," IEEE Transactions on Medical Imaging, vol. 19, No. 8, Aug. 2000.

Maes et al, "Multimodality image registration by maximization of mutual information," IEEE Transactions on Medical Imaging, vol. 16, No. 2, Apr. 1997.

Studholme et al., "An overlap invariant entropy measure of 3D medical image alignment," Pattern Recognition 1 32, 1999, pp. 71-86.

Hansen et al., "A Method for Handling Uncertainty in Evolutionary Optimization With an Application to Feedback Control of Combustion," IEEE Transactions on Evolutionary Computation, vol. 13, No. 1, Feb. 2009, pp. 180-197.

Nelder et al., "A Simplex Method for Function Minimization," The Computer Journal, Jan. 1965, pp. 308-313.

\* cited by examiner

METHOD FOR LOCALIZATION AND IDENTIFICATION OF STRUCTURES IN PROJECTION IMAGES

CROSS-REFERENCE TO RELATED APPLICATION

This application claims the priority, under 35 U.S.C. § 119(e), of U.S. Provisional Patent Application No. 61/485,578 filed May 12, 2011; the prior application is herewith incorporated by reference in its entirety.

BACKGROUND OF THE INVENTION

Field of the Invention

The present invention relates to a method for localization and identification of a structure in a projection image with a system having a known system geometry.

Wrong site surgery is a surprisingly common error in medical practice with major ramification to the patient and healthcare system. It not only results in failure to deliver proper therapy to the patient, but it also has profound medical, legal and social implications. In spinal surgery, for example, the potential for wrong-site surgery (viz., "wrong level" surgery, referring to the level of vertebral body) is significant due to the difficulty of localizing the target vertebrae based solely on visual impression, palpation and fluoroscopic imaging. Vertebrae in the mid-thoracic region can be particularly challenging to localize, since they have fairly similar visual and radiographic appearance and are at a distance from unambiguous anatomical landmarks. A common method to accurately localize a given vertebral level is to "count" vertebrae under fluoroscopy, typically beginning at the sacrum and then "counting" under fluoroscopic visualization up to the targeted vertebral level. Such a method involves an undesirable amount of time and ionizing radiation. Even with fluoroscopic counting, surgery delivered to the wrong level is a fairly frequent occurrence. According to a questionnaire study of 3,505 surgeons, carrying out 1,300,000 procedures, 418 (0.032% or 1 in 3,110) wrong-level spine surgeries were performed [see Mody M G, Nourbakhsh A, Stahl D L, Gibbs M, Alfawareh M, Garges K J., "The prevalence of wrong level surgery among spine surgeons," Spine (Phila Pa. 1976) January 15 33(2), 194-198 (2008)]. Such errors are presumably attributable to foregoing a careful level finding method (e.g., due to time or dose constraints) and/or human errors in counting or otherwise interpreting the fluoroscopic (radiographic) image information (e.g., due to the radiographic similarity between adjacent vertebrae). Several studies [see Perisinakis K, Theocharopoulos N, Damilakis J, Katonis P, Papadokostakis G, Hadjipavlou A, et al., "Estimation of patient dose and associated radiogenic risks from fluoroscopically guided pedicle screw insertion," Spine (Phila Pa. 1976) July 15 29(14), 1555-1560 (2004), and Mariscalco M W, Yamashita T, Steinmetz M P, Krishnaney A A, Lieberman I H, Mroz T E., "Radiation exposure to the surgeon during open lumbar microdiscectomy and minimally invasive microdiscectomy: a prospective, controlled trial," Spine (Phila Pa. 1976) February 1 36(3), 255-260 (2011)] also revealed that the radiation exposure to the surgeon during level localization in spine surgery is a notable issue. Singh et. al. [see Singh H, Meyer S A, Hecht A C, Jenkins A L, 3rd., "Novel fluoroscopic technique for localization at cervicothoracic levels," J. Spinal. Disord. Tech. December 22(8), 615-618 (2009)] proposed to take fluoroscopic images from an oblique direction to facilitate level localization in cervicothoracic spine surgery. The technique helped identifying bony lamina in the image by avoiding interference from chest and shoulders, which can then be used to count spinal levels. Such techniques rely heavily on the surgeon's ability to identify the target level.

SUMMARY OF THE INVENTION

It is accordingly an object of the invention to provide a method for localization and identification of structures in projection images of a body, which overcomes the hereinafore-mentioned disadvantages of the heretofore-known methods of this general type, which significantly decreases the number of wrong-level surgeries and which is independent of the surgeon's ability to localize and/or identify a target level in the body.

With the foregoing and other objects in view there is provided, in accordance with the invention, a method for localization and identification of a structure in a projection image with a system having a known system geometry. The method comprises:
  a) acquiring a preoperative computer-tomography (CT) image of a structure;
  b) preprocessing the CT-image to a volume image;
  c) acquiring an intraoperative two dimensional (2D) X-ray image;
  d) preprocessing the 2D X-ray image to a fix image;
  e) estimating an approximate pose of the structure;
  f) calculating a digitally reconstructed radiograph (DRR) using:
    the volume image,
    the estimated pose and
    the system geometry; and
  g) calculating a correlation between the generated DRR and the fix image, with a correlation value representing matching between the generated DRR and the fix image.

In order to provide a specific illustration of the proposed method, reference is made to the case where the structure to be localized is a vertebra. The structure has been defined (i.e., "segmented") preoperatively in CT, which is referred to as "planning data"), and the 2D images in which the structure (planning data) is to be localized are intraoperative fluoroscopy images obtained on a C-arm. However, the method is fairly general beyond this specific application: the structure could be one or more of any 3D structure(s) of interest, e.g., tumors, anatomical landmarks, vessels, nerves, etc., the structure(s) could be defined in any 3D or 4D image obtained either preoperatively or intraoperatively, and the 2D image in which to localize the structure could be any form of projection image, e.g., fluoroscopy, radiography, or a "projection" MR image. The purpose of the method is to automatically localize (i.e., identify the location of) the structure(s) defined in the 3D image directly within the intraoperative 2D image.

For the specific case of spine surgery and localization of vertebrae ("level finding"), the invention provides information on the target vertebrae location in the intraoperative x-ray image that is acquired with a mobile C-arm. The inventors' initial studies use an intensity-based 3D/2D registration between 3D preoperative CT and 2D intraoperative fluoroscopy, although many variations in the registration technique can be envisioned. By registering the 3D image (in which the structure has been defined preoperatively) to the 2D image, the location of the 3D structure within the 2D image can be automatically computed and displayed to the surgeon.

The invention provides, as an alternative to the state of the art, a method for automatic localization of predefined 3D structures (e.g., vertebrae) in 2D fluoroscopic/radiographic images using 3D-2D registration. 3D/2D registration between preoperative CT and X-ray projections has been explored extensively [see Markelj P, Tomaževič D, Likar B, Pernuš F., "A review of 3D/2D registration methods for image-guided interventions," Med. Image Anal. In Press, Corrected Proof], e.g., in radiation therapy, with the goal of registering between the patient and the treatment plan. An intensity-based method is one of the prospective approaches to improve the accuracy of 3D/2D registration by using all image information as opposed to a feature-based method. Two commercial radiotherapy systems, CyberKnife® Robotic Radiosurgery System (Accuray Incorporated, Sunnyvale, Calif.) [see Fu D, Kuduvalli G., "A fast, accurate, and automatic 2D-3D image registration for image-guided cranial radiosurgery," Med. Phys. May 35(5), 2180-2194 (2008)] and Novalis® (BrainLAB AG, Feldkirchen, Germany) [see Agazaryan N, Tenn S E, Desalles A A, Selch M T., "Image-guided radiosurgery for spinal tumors: methods, accuracy and patient intrafraction motion," Phys. Med. Biol. March 21 53(6), 1715-1727 (2008)], employ intensity-based 3D/2D registration for purposes and methods quite distinct from those proposed herein. Those algorithms are provided for a dedicated linear accelerator which has precise motorized-controlled rotation and thus, multiple accurately calibrated images are available. On the contrary, fixed and mobile C-arms, which are increasingly common to surgery and interventional radiology, can be difficult to use for providing precise intrinsic and extrinsic calibration due to the nature of mechanical instability.

Other features which are considered as characteristic for the invention are set forth in the appended claims.

Although the invention is illustrated and described herein as embodied in a method for localization and identification of structures in projection images, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
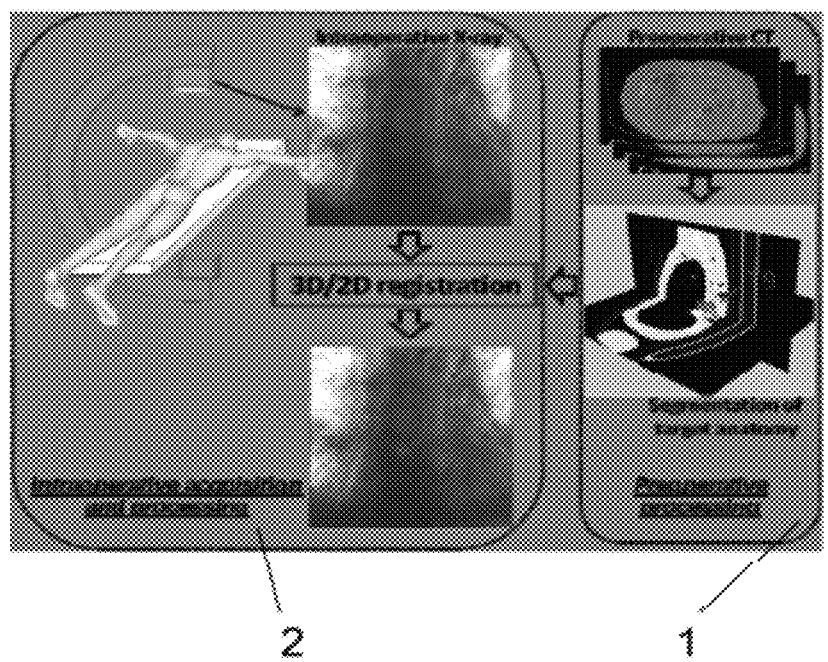
FIG. 1 is a flowchart showing an overview of a system for carrying out the method according to the invention, including preoperative and intraoperative steps.

Referring now to the figures of the drawings in detail and first, particularly, to FIG. 1 thereof, there is seen a system for carrying out a method which includes a preoperative step 1, wherein a CT image of another volumetric image is taken. Projection data is derived from this image by computing. An intraoperative step 2 includes an acquisition of a 2D X-Ray image.

Figure 2:
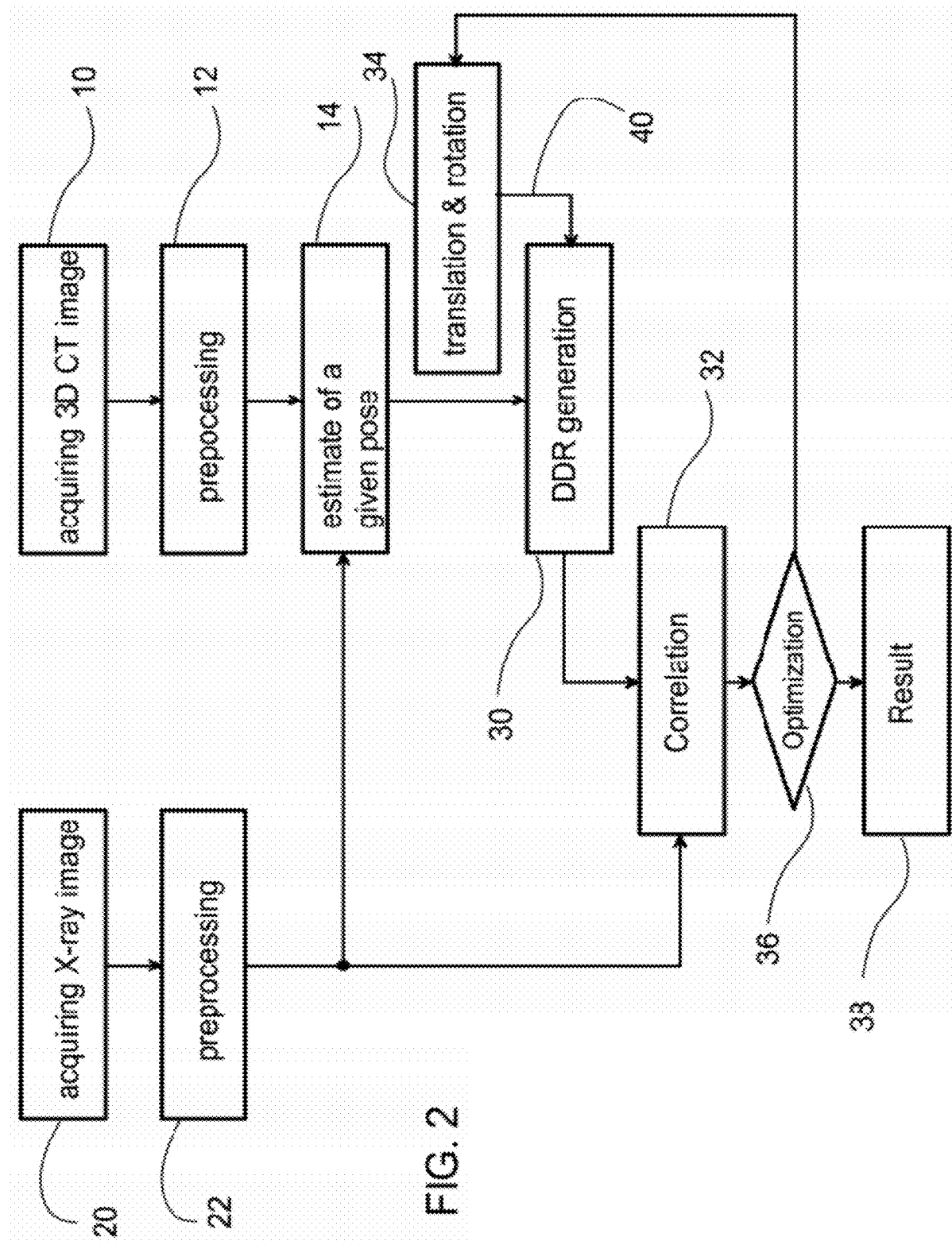
FIG. 2 is a flowchart showing method steps for localization and identification of structures in projection images.

Reference is made to FIG. 2 for showing an example of the proposed workflow for localization and identification of a structure in a projection image.

1. Preoperative Processing 1.1 Acquisition and Preprocessing of Preoperative CT Data A preoperative 3D image provides the basis for 3D-2D registration. The preoperative image could be a CT image (which is preferred) or another volumetric image modality from which projection data may be computed.

In a step 10, a preoperatively acquired diagnostic CT, represented in Hounsfield Units (HU), is converted into a volume image represented by a linear attenuation coefficient based on the following definition [see Prince J L, Links J M. Medical Imaging Signals and Systems. Upper Saddle River, N.J.: Pearson Prentice Hall; 2006]:

$$\mu = \left(\frac{1000+HU}{1000}\right)\mu_{water} \qquad (1)$$

where $\mu$ is the linear attenuation coefficient of the voxel and $\mu_{water}$ is the coefficient of water at the X-ray energy which was used for the CT scanning.

1.2 Segmentation of the Preoperative CT Data

The target anatomical structure is segmented. The segmentation can be done by either:

i) delineating target anatomy manually or by any variety of automatic or semiautomatic segmentation approaches;

ii) identifying simply the point within the target structure that is to be projected in a (e.g., the anterior-posterior (AP)) projection image at the approximate center of the projected target anatomy. This segmentation step is depicted as preprocessing in a step 12 in FIG. 2.

2. Acquisition and Preprocessing of Intraoperative X-Ray Image

The intraoperatively acquired 2D x-ray projection image is preprocessed to obtain a line integral of a linear attenuation coefficient from 2D image intensity values ($I_d$). The line integral of the linear attenuation coefficient is represented as:

$$g_d = \int_0^d \mu(s)ds = -\ln(I_d/I_0) \qquad (2)$$

where the middle term represents the integral along a line connecting the x-ray source and the detector element, $I_d$ is the image intensity at the detector, and $I_0$ is the intensity of the unattenuated beam [see Prince J L, Links J M. Medical imaging signals and systems. Upper Saddle River, N.J.: Pearson Prentice Hall; 2006]. $I_0$ is defined by using the intensity of a pixel in the area with no visible object. These are steps 20 and 22 in FIG. 2.

3. 3D/2D Registration

The further workflow of the 3D/2D registration in the proposed system is shown in FIG. 2 as follows:

Firstly: estimation of an approximate pose between preoperative CT and intraoperative X-ray projection as an initial estimate for optimization according to step 14.

The estimate does not need to be accurate. The approximate pose could be induced from a surgical protocol, which usually indicates the position of the patient on the operating table with respect to the imager (e.g. supine position, prone position, etc.). Then, using the estimated pose and known system geometry, a digitally reconstructed radiograph (DRR) is generated, for example by using graphical processing unit (GPU)-acceleration, as is seen from step 30 in FIG. 2.

The generated DRR and fixed image preprocessed X-ray projection images are compared by a similarity measure, e.g., mutual information (MI) or (inverse) sum-of-squared-differences (SSD) between the two 2D images. The term "fixed" image is a fairly standard term in image registration. It refers to the image "onto" which one is registering. The following comparison may include or replace a correlation, seen in step 32 in FIG. 2.

The estimated pose is repeatedly updated so that the similarity increases in the optimizer.

When a criterion of optimization in a step 36 is reached, the pose will be displayed as a result in a step 38.

One possible similarity measure that can be used here is gradient information proposed by Pluim et. al. [see Pluim J P, Maintz J B, Viergever M A., "Image registration by maximization of combined mutual information and gradient information," IEEE Trans. Med. Imaging August 19(8), 809-814 (2000)]. However, the method is equally applicable with other similarity measures including mutual information [see Maes F, Collignon A, Vandermeulen D, Marchal G, Suetens P., "Multimodality image registration by maximization of mutual information," IEEE Trans. Med. Imaging April 16(2), 187-198 (1997)], normalized mutual information [see Studholme C, Hill D L G, Hawkes D J., "An overlap invariant entropy measure of 3D medical image alignment," Pattern Recognit 1 32(1), 71-86 (1999)], etc. Similarly, a variety of optimization methods can be used, e.g., the inventors used a CMA-ES algorithm [see Hansen N, Niederberger A S P, Guzzella L, Koumoutsakos P., "A Method for Handling Uncertainty in Evolutionary Optimization With an Application to Feedback Control of Combustion," Evolutionary Computation, IEEE Transactions on 13(1), 180-197 (2009)] as an optimizer, but any other optimizer is applicable, including Nelder-Mead downhill simplex [see Nelder J A, Mead R., "A Simplex Method for Function Minimization," The Computer Journal January 1 7(4), 308-313 (1965)], etc.

Although much of the description above describes a mobile C-arm imager, the concept is equally applicable to implementations on other imaging or therapeutic devices, including:

- a ceiling-mounted or floor-mounted C-arm for fluoroscopy or cone-beam CT;
- a table-integrated radiography/fluoroscopy system;
- a mobile x-ray radiography system;
- a radiation therapy linear accelerator gantry, robotic radiotherapy device, or radiotherapy simulator.

Similarly, target structures/anatomy are not confined to the spine. Such could be equally useful in other areas where intraoperative x-ray images are used in a clinical routine for "searching" to localize a structure. This includes guidance for:

- other anatomical structures, including bones, vessels, nerves;
- implanted devices visible in preoperative images, e.g., stents, catheters, implants, etc.;
- orthopedic surgery as a means for a simpler alternative for an advanced navigation system;
- a variety of catheter procedures for guiding the tip of catheter with respect to the planning data;
- an endoscopic surgery (e.g. NOTES).

Although an exemplary embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope, rather the scope of patented subject matter is defined only by the allowed claims.

The invention claimed is:

1. A method for localization and identification of a vertebra with a system having a known system geometry, the method comprising the following steps:
    a) acquiring a preoperative 3D computer-tomography (CT) image of a vertebra;
    b) preprocessing the 3D CT image to generate a volume image by segmenting the vertebra in the 3D CT image;
    c) acquiring an intraoperative two dimensional (2D) X-ray image;
    d) preprocessing the 2D X-ray image to obtain a line integral of a linear attenuation coefficient from 2D image intensity values to generate a fixed image;
    e) estimating an approximate pose of the vertebra;
    f) calculating a digitally reconstructed radiograph (DRR) using:
        the volume image,
        the estimated approximate pose and
        the system geometry;
    g) comparing the calculated DRR and the fixed image by similarity measure based on gradient information;
    h) updating the estimated approximate pose in order to increase the similarity measure;
    i) repeating steps f) to h) until the similarity measure reaches a criterion of optimization and then displaying the estimated approximate pose to represent a localized and identified vertebra, wherein in each repetition of step f), the updated estimated approximate pose that was previously calculated in a most recent performance of step h) is used as the estimated approximate pose; and
    j) overlaying the calculated DRR from a last repetition of step f) onto the fixed image in order to compute a location of the localized and identified vertebra within the fixed image, and displaying the location of the localized and identified vertebra within the fixed image.

2. The method according to claim 1, wherein the calculated DRR is processed by a translation and/or rotation when repeating steps f) to g).

3. The method according to claim 1, which further comprises acquiring the 2D X-Ray image or the 3D CT image with a C-arm device.

* * * * *